US00PP09665P

United States Patent [19]

Olesen et al.

[11] Patent Number: Plant 9,665

[45] Date of Patent: Oct. 22, 1996

[54] SHRUB ROSE PLANT NAMED 'POULPYG'

[75] Inventors: Pernille Olesen; Mogens Olesen, both of Fredensborg, Denmark

[73] Assignee: DeVor Nurseries, Inc., Watsonville, Calif.

[21] Appl. No.: 414,905

[22] Filed: Mar. 31, 1995

[51] Int. Cl.[6] ..... A01H 5/00

[52] U.S. Cl. ..... Plt./1

[58] Field of Search ..... Plt./1, 22, 24

*Primary Examiner*—Howard J. Locker

*Attorney, Agent, or Firm*—Christie, Parker & Hale, LLP

[57] ABSTRACT

A shrub rose variety producing peach colored flowers.

1 Drawing Sheet

SUMMARY OF THE INVENTION

The present invention relates to a new and distinct shrub rose variety which was originated by our crossing as seed and pollen parents two unnamed and undistributed seedlings of our creation. The varietal denomination of this new rose is 'Poulpyg'.

Among the novel characteristics possessed by this new variet which distinguish it from its parents and all other varieties of which we are aware are its attractive peach flowers borne on a floriferous bushy, vigorous plant useful in landscaping.

Asexual reproduction by budding of the new variety as performed in Watsonville, Calif., shows that the foregoing and other distinguishing characteristics come true to form and are established and transmitted through succeeding propagations. Other known forms of asexual reproduction may be also employed.

BRIEF DESCRIPTION OF ILLUSTRATIONS

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—Unnamed, unpatented seedling.

*Pollen parent.*—Unnamed, unpatented seedling.

Class: Shrub.

The following is a detailed description of the new variety, from specimens grown outdoors in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

FLOWER

Blooming habit: Recurrent.

A. Bud:

(1) *Size.*—Small, about 1.1 cm long by about 1 cm wide.

(2) *Form.*—Ovoid.

(3) *Color.*—When sepals first divide, bud color is near 29C with peach/apricot shading toward the apex of the bud extending downwrdly.

(4) *Sepals.*—About 1 cm long, spread and reflex when bloom opens; some sepals are foliaceous. Color: Near 144B.

(5) *Peduncle.*—Length: About 3 to about 4½ cm. Aspect: Very small prickles. Strength: Erect, sturdy, slender. Color: Near 144B.

(6) *Bracts.*—About 1 to 10 in a bunch of 3 to 11 blooms; near 137A; about 1½ to 2 cm below calyx.

B. Bloom:

(1) *Size.*—Average size when fully expanded — about 3½ cm to about 4½ cm.

(2) *Borne.*—Clusters of about 3 to 11 blooms.

(3) *Form.*—Imbricated, balling in center, reflex at maturity. becomes somewhat informal.

(4) *Petalage:*—Number of petals under normal conditions — about 26 to 30.

(5) *Color* (⅓ to ½): Outer petals — are near white to cream with shading near 55C to 55D; Undersurface: White to cream edged near 55C on top fading to near 29D. Inner Petals — Top Surface: Top is near 29D; Undersurface: near 29D; white, near 11B toward base. Base of petals — (point of attachment): Near 4A. General tonality from a distance: Apricot.

(6) *Color (fully open).*—Top surface: near white with slight pink shading on outer petals and cream color when petals bunch. General tonality from a distance: Apricot.

(7) *Color change.*—As bloom ages: Color lightens to near white coloration. Petal top surface: Lightens. Petal undersurface: Lightens. General tonality at a distance: Fades to light pink.

C. Petals:

(1) *Texture.*—Thick.

(2) *Appearance.*—Inside slightly velvety and outside matte.

(3) *Form.*—Wedge shaped with some notched petals.

(4) *Arrangement.*—Imbricated.

(5) *Petaloids.*—Few.

(6) *Fragrance.*—Slight musk.

(7) *Lasting quality.*—Not a cut flower variety; lasts about 9 to 11 days on plant.

(8) *Persistence.*—Petals drop off cleanly.

REPRODUCTIVE ORGANS

A. Stamens:

(1) *Arrangement.*—Introrse, regularly arranged around styles.

(2) Anthers.—Near 15B.

(3) *Filaments.*—Near 2A.

(4) *Pollen.*—Near 15B.

B. Pistils:

(1) *Styles.*—Bunched.
(2) *Stigmas.*—Near 4C at tip, balance near 60C with near 4C at base.

C. Characteristics of hips: Not observed.

PLANT

A. Form: Compact, low growing.
B. Growth: Very vigorous; about 38 cm to about 51 cm in height and width at first season.
C. Foliage: Some compound 3 and 7 leaflets but mostly compound 5 leaflets.
(1) *Size.*—Small.
(2) *Quantity.*—Abundant.
(3) *Color.*—New Foliage — upper side near 147A; underside near 147B; mature foliage — upper side near 147A, underside near 147B.
(4) *Shape.*—Ovate.
(5) *Texture.*—Upper side slightly leathery, smooth; underside slightly leathery.
(6) *Edge.*—Serrate.
(7) *Serration.*—Denticulate.
(8) *Leaf steam.*—Color — medium green.
(9) *Stipules.*—Adnate, small glands on edges, parallel, broader at base then narrowing.
(10) *Rachis.*—Small prickles along with some thorns on underside.
(11) *Petioles.*—Top near 146B, underside near 143C.
(12) *Auricle.*—Thin, tipped, spreading outwardly.
(13) *Resistance to disease.*—Very resistant to blackspot, and rust, medium resistance to mildew.
D. Wood:
(1) *New wood.*—Color near 143C, bark smooth.
(2) *Old wood.*—Color near 137A, bark smooth.
E. Flower stem: About 17 cm to about 28 cm from last cut.
F. Thorns:
(1) *Thorns.*—Quantity: On main stalk, average; laterals from stalk, average. Form: Slightly curved downward, wing-shaped base. Length: Medium. Color: Near 165A. Position: Irregular.
(2) *Prickles.*—None.
G. Winter hardiness: Winter hardy in Denmark and in Watsonville, Calif.

I claim:

1. A new and distinct shrub rose plant variety, substantially as shown and described.

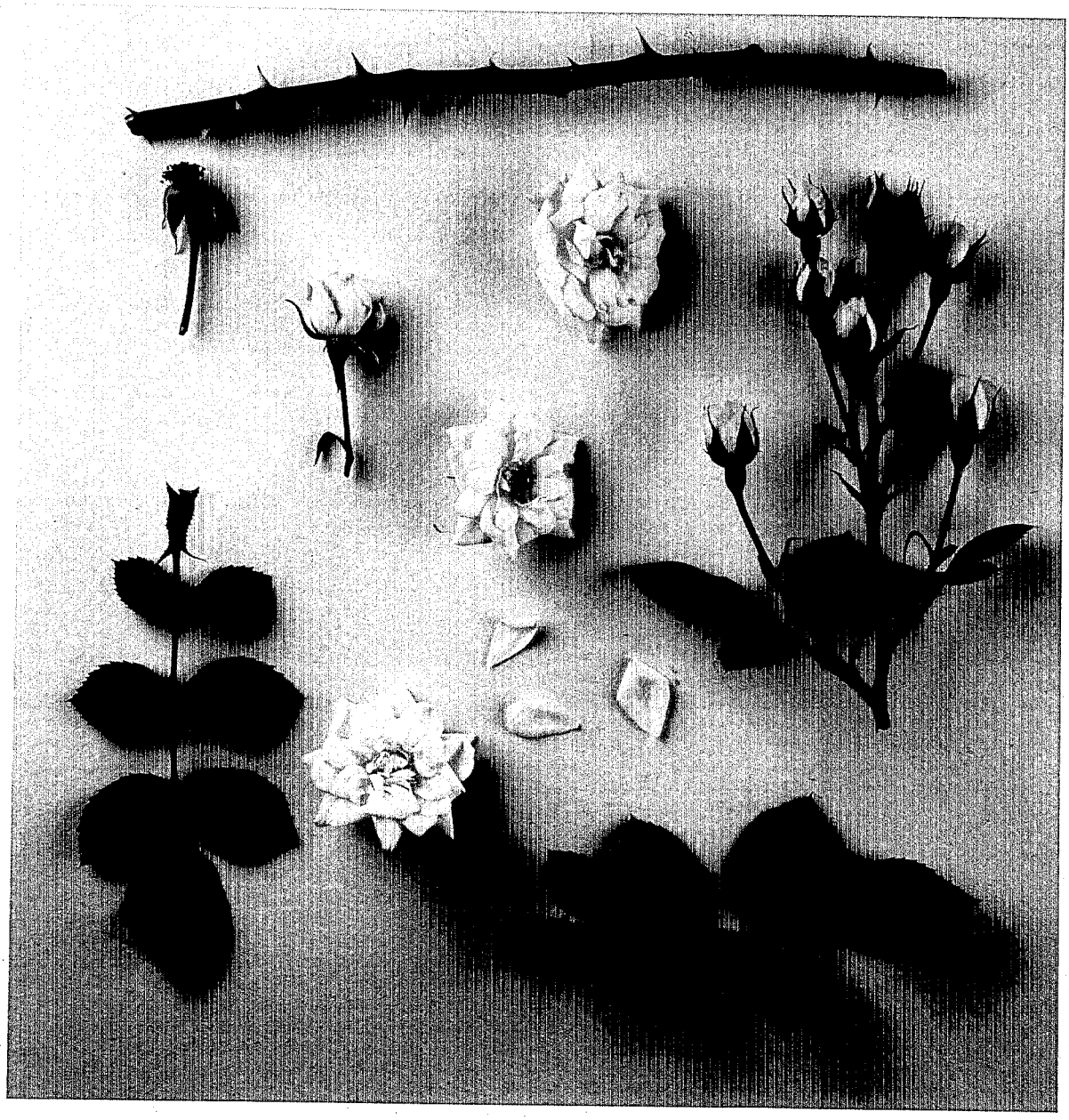

* * * * *